US005637877A

United States Patent [19]
Sinofsky

[11] Patent Number: 5,637,877
[45] Date of Patent: Jun. 10, 1997

[54] ULTRAVIOLET STERILIZATION OF INSTRUMENT LUMENS

[75] Inventor: Edward L. Sinofsky, Dennis, Mass.

[73] Assignee: Rare Earth Medical, Inc., W. Yarmouth, Mass.

[21] Appl. No.: 471,744

[22] Filed: Jun. 6, 1995

[51] Int. Cl.⁶ .................................. A61L 2/08; B08B 9/00
[52] U.S. Cl. .......................... 250/492.1; 422/24; 606/15
[58] Field of Search ............................ 250/492.1; 606/7, 606/15; 128/303.1; 422/24

[56] References Cited

U.S. PATENT DOCUMENTS

| Re. 34,544 | 2/1994 | Spears | 604/20 |
|---|---|---|---|
| 3,417,745 | 12/1968 | Sheldon | 128/6 |
| 4,233,493 | 11/1980 | Nath | 219/354 |
| 4,336,809 | 6/1982 | Clark | 128/665 |
| 4,585,298 | 4/1986 | Mori | 350/96.1 |
| 4,660,925 | 4/1987 | McCaughan, Jr. | 350/96.15 |
| 4,860,743 | 8/1989 | Abela | 128/303.1 |
| 4,861,727 | 8/1989 | Hauenstein et al. | 436/136 |
| 4,878,492 | 11/1989 | Sinofsky et al. | 128/303.1 |
| 5,053,033 | 10/1991 | Clarke | 606/3 |
| 5,116,317 | 5/1992 | Carson et al. | 604/96 |
| 5,133,709 | 7/1992 | Prince | 606/7 |
| 5,151,096 | 9/1992 | Khoury | 606/15 |
| 5,151,097 | 9/1992 | Daikuzono | 606/15 |
| 5,168,863 | 12/1992 | Kurtzer | 128/4 |
| 5,169,395 | 12/1992 | Narciso, Jr. | 606/7 |
| 5,196,005 | 3/1993 | Doiron et al. | 606/7 |
| 5,207,669 | 5/1993 | Baker et al. | 606/7 |
| 5,209,748 | 5/1993 | Daikuzono | 606/16 |
| 5,219,346 | 6/1993 | Wagnières et al. | 606/16 |
| 5,240,675 | 8/1993 | Wilk et al. | 422/22 |
| 5,242,438 | 9/1993 | Saadatmanesh et al. | 606/15 |
| 5,269,777 | 12/1993 | Doiron et al. | 606/7 |
| 5,337,381 | 8/1994 | Biswas et al. | 385/36 |
| 5,363,458 | 11/1994 | Pan et al. | 385/31 |
| 5,401,270 | 3/1995 | Müller et al. | 606/13 |
| 5,405,369 | 4/1995 | Selman et al. | 605/88 |
| 5,431,647 | 7/1995 | Purcell, Jr. et al. | 606/16 |
| 5,441,497 | 8/1995 | Narcisco, Jr. | 606/15 |

FOREIGN PATENT DOCUMENTS

| 0214712 | 3/1987 | European Pat. Off. |
| 0292695 | 11/1988 | European Pat. Off. |
| 0292621A1 | 11/1988 | European Pat. Off. |
| 0439629 | 8/1991 | European Pat. Off. |
| 0439629A1 | 8/1991 | European Pat. Off. |
| 0598984 | 6/1994 | European Pat. Off. |
| WO92/17243 | 10/1992 | WIPO . |
| WO93/06888 | 4/1993 | WIPO . |
| WO93/19680 | 10/1993 | WIPO . |
| WO93/25155 | 12/1993 | WIPO . |
| WO94/17434 | 8/1994 | WIPO . |

OTHER PUBLICATIONS

U.S. Ser. No. 303,605, Simofsky, filed Sep. 9, 1994.

Primary Examiner—Bruce C. Anderson
Attorney, Agent, or Firm—Thomas J. Engellenner; Lahive & Cockfield

[57] ABSTRACT

Methods and devices are disclosed for sterilization of endoscopic instrument lumens. Diffuse ultraviolet radiation is employed to sterilize the inner surfaces of the instrument lumen. The ultraviolet radiation can be delivered via one or more optical fibers having a light-diffusing assembly coupled thereto. The instrument operates by delivering cytotoxic radiation to the inner lumen surface to sterilize any biological agents which may be present within the instrument lumen.

12 Claims, 1 Drawing Sheet

ULTRAVIOLET STERILIZATION OF INSTRUMENT LUMENS

BACKGROUND OF THE INVENTION

The technical field of this invention is medical instrumentation and, in particular, methods and apparatus for sterilizing medical instrument lumens.

Endoscopic instruments are complex and expensive medical devices, which permit the clinician to view the internal organs and structures of a patient's body. These instruments are typically reused and, therefore, must be sterilized after each use. Moreover, because many endoscopes are used repeatedly throughout a day, sterilization of the instruments must be performed rapidly in busy clinics.

Conventionally, endoscopes are sterilized using a chemical bath. The internal lumens of the instrument will either be soaked in a sterilizing liquid or flushed with the sterilizing liquid.

Unfortunately, conventional techniques can sometimes be less than totally effective. The sterilizing liquid may not penetrate the entire lumen or may not be sufficiently strong to achieve the desired antimicrobial effect. Moreover, the endoscope lumen may have accumulated cellular debris that cannot be simply flushed out and such debris may harbor microbes that are not destroyed in the cleaning process.

Accordingly, there exists a need for better methods and devices for sterilizing the inner lumens of endoscopic instruments. Methods and devices which could ensure more effective anti-microbial action and/or permit more rapid sterilization of instrument lumens, would satisfy a long-felt need in the art.

SUMMARY OF THE INVENTION

Methods and devices are disclosed for sterilization of endoscopic instrument lumens. Diffuse ultraviolet radiation is employed to sterilize the inner surfaces of the instrument lumen. The ultraviolet radiation can be delivered via one or more optical fibers having a light-diffusing assembly coupled thereto. The instrument operates by delivering cytotoxic radiation to the inner lumen surface to sterilize any biological agents which may be present within the instrument lumen.

In one aspect of the invention a lumen sterilizing apparatus is disclosed having a light transmitting fiber which is capable of transmitting ultraviolet radiation. The apparatus further includes a diffuser means, coupled to the fiber for diffusing ultraviolet radiation from the fiber. The fiber and diffuser are sufficiently small so as to fit within an endoscope lumen. The apparatus further includes an irradiation means for generating ultraviolet radiation and for coupling the radiation to the fiber.

The sterilizing ultraviolet radiation preferably ranges from about 400 to about 200 nanometers in wavelength and, more preferably, from about 300 to 220 nanometers, and most preferably, from about 280 to 240 nanometers. Such radiation can be obtained from a laser source, such as an Argon ion laser or an excimer laser (such as a Xenon Chloride excimer laser). Alternatively, a solid state laser can be used in conjunction with frequency modifying element. For example, an infrared radiation source can be used in conjunction with two frequency-doubling crystals, which cooperate to yield a frequency-quadrupled radiation beam in the ultraviolet spectrum. In yet another alternative embodiment, a simple ultraviolet flash lamp can be employed as the light source and coupled to the optical fiber.

The optical fiber can be any conventional optic transmission element including, for example, fused silica. As used herein, the term "optical fiber" is intended to encompass optically transmissive wave guides of various shapes and sizes.

In one embodiment, a diffusing tip can be employed in conjunction with the optical fiber to deliver diffuse cytotoxic radiation to the inner lumen. The diffusive fiber tip structure can be formed by radiation-scattering particles carried in a suitable transmission medium. For example, the optically transmissive fiber tip can be a cylindrical structure fitted to the distal end of the optical fiber and further fitted with a reflective end cap. As radiation propagates through the fiber tip, a portion of the radiation is scattered. Each time the radiation encounters a scatterer particle, it is deflected until some of the radiation exceeds the critical angle for internal reflection and exits the tip. Radiation which is not emitted during this initial pass through the tip is reflected by at least one end surface and return through the tip. During the second pass the remaining radiation (or at least a major portion of this returning radiation) again encounters the scatterers which provide further radial diffusion of the radiation.

In another embodiment, the diffusing tip can be constructed from a tubular element filled with any suitable medium that diffuses light without the need for particulate scatterers. For example, a longer tube filled with water or acetic acid can also serve as the scattering medium. In this embodiment it may not be necessary to move the diffusing tip. Instead, the apparatus can be used to sterilize a substantial portion, or the entire length, of the lumen all at once.

In another aspect of the invention, novel materials and structures are disclosed for diffusive tip assemblies which further alleviate or reduce the potential for contact-adhesion between the tip and the nearby lumen wall. This aspect of the invention is particularly useful to ensure that the diffusive tip does not accidentally bond to the instrument lumen or debris within the lumen. In one embodiment, fluoropolymer materials, such as Teflon® materials and the like are disclosed as preferred materials for the tip enclosure because of their low contact-adhesion characteristics, deep ultraviolet transmissivity and ion refractive index.

In yet another aspect of the invention, disposable sheaths are disclosed for use in conjunction with the ultraviolet sterilizing fiber and diffuser assembly. The outer sheath surrounds the entire optical transmission apparatus and ensures that the radiation-generating components do not come into direct contact with the instrument lumen or the debris which may be present in such lumen. This permits reuse not only of the endoscope repeatedly by a clinician, but also reuse of the sterilizing instrument. Only the sheath surrounding the sterilization apparatus need to be disposed after each use. Alternatively, a disposable sheath/diffuser can be used in conjunction with a reusable fiber. Thus, a disposable sheath filled with a light scattering medium can be fitted to a reusable fiber and then used to perform instrument sterilization. When the procedure is completed, the sheath and the scattering medium inside can then be discarded.

In a further aspect of the invention, methods are disclosed for performing instrument sterilization. These methods typically involve the placement of an ultraviolet radiation-diffusing assembly within the endoscopic instrument lumen and then the pulling of the sterilization apparatus through the lumen such that the entire inner surface is bathed with cytotoxic radiation. The method can further include the use of a disposable outer sheath which surrounds the sterilization apparatus while it is being pulled through the lumen and then is discarded after the sterilization procedure is completed.

The terms "endoscopic instrument" and "endoscope" are used herein to describe a general class of instrument useful in viewing internal body structures or performing operations within a patient's body, including cystoscopes, tracheoscopes, culpascopes, proctoscopes, laprascopes, catheters, arthroscopes, other endoscopes and the like.

The invention will next be described in connection with certain illustrated embodiments. However, it should be clear that various changes and modifications can be made by those skilled in the art without departing from the spirit or scope of the invention.

BRIEF DESCRIPTION OF THE DRAWINGS

The invention may be more fully understood from the following description when read together with the accompanying drawings in which.

DETAILED DESCRIPTION

Figure 1:
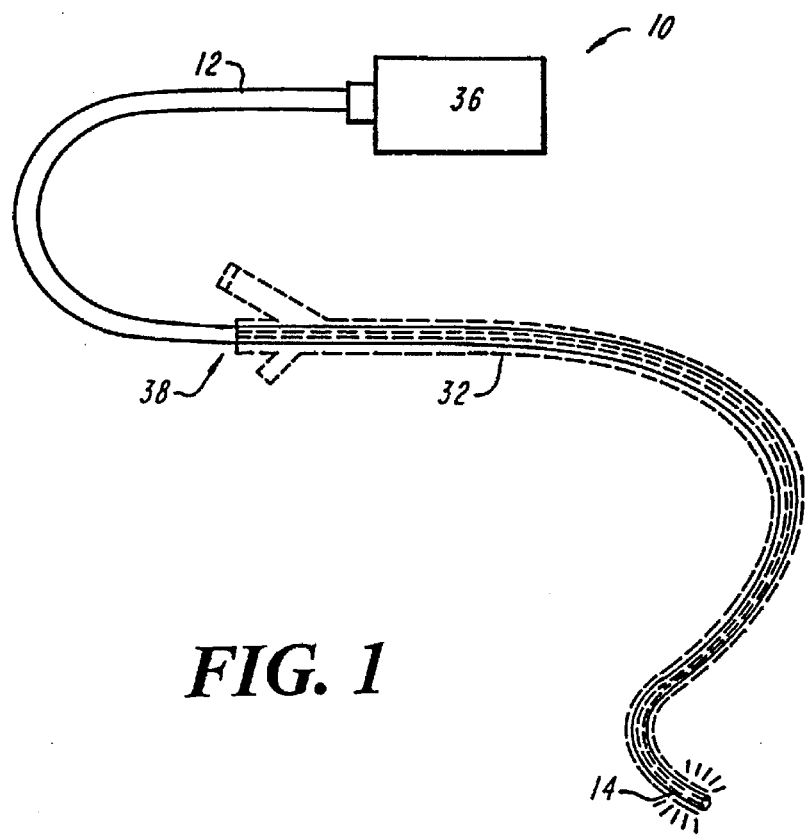
FIG. 1 is a schematic view of an apparatus for sterilization of medical instruments according to the invention.

In FIG. 1 an apparatus 10 for sterilizing an inner lumen of an endoscopic medical instrument 32 is shown including a source of ultraviolet radiation 36, an optical fiber 12 and a diffusive tip assembly 14.

In use, the apparatus 10 serves to sterilize or clean an inner lumen of the endoscopic instrument 32. The optical fiber 12 with its light-diffusing distal tip assembly 14 is inserted into the lumen requiring sterilization. In one technique, the optical fiber tip can be inserted through the entire instrument and then slowly retracted. The radiation source is activated to transmit light via the fiber 12 to the diffusive tip assembly 14. As the apparatus is retracted through the endoscope lumen 38, cytotoxic radiation is delivered to all portions of the inner lumen walls. Any debris or deposits on the inner lumen walls are likewise irradiated to kill any microbes which may be harbored in such deposits.

Figure 2:
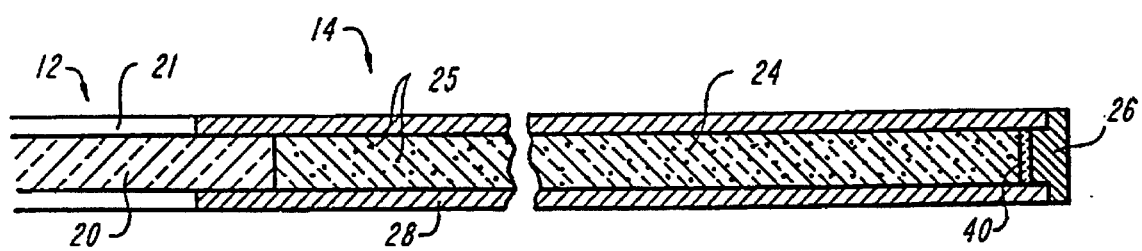
FIG. 2 is a cross-sectional view of an optical fiber diffusive tip assembly for use in the sterilization apparatus of FIG. 1.

In FIG. 2 a diffusive tip assembly 14 is shown in more detail proving the optical fiber 12 having a light transmissive core 20 and a buffer coating or cladding 21. The end face of fiber core 20 is inserted into a housing 28 which contains a scattering medium 24 with optional individual scattering particles 25. Preferably, the medium 24 has a greater refractive index than the housing 28. At the distal end of the housing 28, an end plug 26 is disposed with a mirror reflector 40.

Light propagating through the optical fiber core 20 is transmitted into the scatterer medium 24 and scattered in a cylindrical pattern along the length of the assembly 14. Each time the light encounters a scatterer particle, it is deflected and, at some point, the net deflection exceeds the critical angle for internal reflectance at the interface between the housing 28 and the medium 24. When this happens, the light will exit. Light which does not exit during the initial pass through the tip is reflected by the mirror 28 and returned through the tip assembly. During the second pass, the remaining radiation (or at least the major portion of this returning radiation) again encounters the scatterers 25 which provide further circumferential diffusion of the ultraviolet light.

Various other diffusive tip assemblies can be employed in the present invention. For a detailed discussion of various alternative embodiments, see commonly-owned, co-pending U.S. patent application Ser. No. 08/303,605 filed Sep. 9, 1994 entitled "Phototherapy Methods And Apparatus" by Edward L. Sinofsky as well as commonly-owned, co-pending patent application entitled "Loop Diffuser For Diffusion Of Optical Radiation" by Edward L. Sinofsky, filed of even date herewith (Attorney Docket No. ROE-024) both of which are incorporated herein by reference.

The optimal concentration of scatterer particles incorporated into this scatterer medium will, of course, vary with the diameter of the tube, the length of the tube and the wavelength as well as other factors. Nonetheless, an optimal concentration can readily be determined empirically for ultraviolet radiation in the range of about 400 nanometers to about 200 nanometers, one preferred composition for the scatterer medium is colloidal alumina suspended in acetic acid. It should also be appreciated that the length of the scatterer tube (e.g., the distance between the fiber end facing and the reflector) will also affect the uniformity of the diffused radiation.

In one preferred embodiment of the invention, the scatterer concentration and mirror location are chosen such that light is diffused in a substantially uniform axial pattern. The reflective surface located at the distal end of the instrument can, for example, be an aluminum or dielectric coated reflective mirror. The outer housing for the diffusive tip is preferably a Teflon® FEP tubular housing (having an outer diameter of about 0.5 millimeters and an inner diameter of about 0.25 millimeters).

An exemplary manufacturing process suitable for joining the diffuser assembly to a glass-clad or polymer-clad optical fiber having an outer diameter of about 50 to 1,000 micrometers can begin by stripping off the buffer from the end of the fiber, e.g., exposing about 2 or 3 millimeters of the inner fiber core and its cladding. (It is not necessary to strip the cladding away from the core.) Prior to stripping, the fiber end face preferably should be prepared and polished as is known in the art to minimize boundary or interface losses.

A transparent tubular structure which will form the housing for the scatterer medium can then be slid over the prepared fiber end and, preferably, slid beyond the fiber end. For example, if the tip assembly is about 20 millimeters, the tubing can be about 100 millimeters long and slid over about 75 millimeters of the fiber, leaving an empty lumen of about 25 millimeters in front of the fiber end face. In one preferred embodiment, the housing is a Teflon® FEP tubing available, for example, from Zeus Industries (Raritan, N.J.). The transmission spectrum of Teflon® FEP shows that this material is well suited for a scatterer encasing material across a spectrum of light ranging from the infrared to ultraviolet.

Once the transparent tubular structure is slid over the optical fiber, the assembly is then ready for injection with a scatterer loaded material. Following loading with the scatterer medium, a reflective tip end cap can be fitted to the distal end of the housing. Alternatively, the tubular structure can be constructed with an integral end cap, slid into place over the fiber and then filled via a syringe through a minute hole in the end cap or the tubular housing. In yet another alternative, the tubular structure can be formed with the end cap and filled with the scattering medium before being slid over the fiber.

Figure 3:
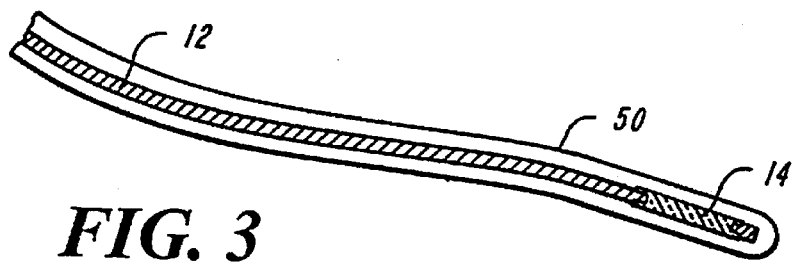
FIG. 3 is a cross-sectional view of an optical fiber and diffusive tip assembly in accordance with the present invention, further employing a disposable outer sheath.

Optionally, as shown in FIG. 3, an outer Teflon® jacket can be disposed about the apparatus as a final step to encase and protect the entire tip assembly including the inner scatterer tube and fiber end.

It should be clear that the manufacturing processes described are merely illustrative, and various alternative techniques can be practiced to construct a fiber tip assembly of the present invention. For example, automated extrusion processes and/or injection molding approaches can be employed to mass produce fibers with integrated diffusive tip assemblies.

In use, the apparatus is slid into an endoscope lumen and connected to a UV light source. The light source is activated and the UV radiation is transmitted to the diffusive tip, where the scatterers project a cylindrical exposure pattern to the lumen walls. The apparatus can then be slid forward or backwards (or in both directions) to bathe the entire lumen with sterilizing irradiation.

I claim:

1. Apparatus for sterilizing an endoscopic instrument lumen comprising:

a light delivery fiber for receiving ultraviolet (UV) radiation at a proximal end and sufficiently small to fit within an endoscopic instrument lumen and transmit the UV radiation through the lumen;

a diffuser optically coupled to a distal end of the fiber for diffusing UV radiation from said fiber onto the inner wall surface of a instrument lumen, the diffuser comprising a light scattering medium into which the UV radiation is transmitted such that upon placement of the apparatus within an endoscopic instrument lumen and coupling of the fiber with a UV radiation source, radiation is transmitted through the fiber and deflected radially outwardly by the scattering medium to irradiate and sterilize the lumen; and a disposable sheath adapted to surround the diffuser and at least part of the light delivery fiber.

2. The apparatus of claim 1 wherein the light delivery fiber is a fused silica fiber.

3. The apparatus of claim 1 wherein the diffuser further comprises a fluoropolymer housing containing a scattering medium.

4. The apparatus of claim 1 wherein the apparatus further comprises a source of radiation.

5. The apparatus of claim 4 wherein the source of radiation is a source of UV radiation in the range of about 400 to about 200 nanometers.

6. The apparatus of claim 5 wherein the source of radiation is an Argon ion laser.

7. The apparatus of claim 5 wherein the source of radiation is an excimer laser.

8. The apparatus of claim 5 wherein the source of radiation is a frequency multiplied solid state laser.

9. The apparatus of claim 4 wherein the source of radiation is an ultraviolet flash lamp.

10. A method for sterilizing an endoscopic instrument lumen comprising:

surrounding a light delivery fiber capable of transmitting UV radiation and having a diffusive tip assembly at the fiber's distal end for diffusing UV radiation with a disposable sheath;

introducing the sheathed light delivery fiber and diffusive tip assembly into a lumen of an endoscopic instrument, the diffusive tip assembly comprising a light scattering medium into which the UV radiation is transmitted such that upon coupling of the fiber with a UV radiation source, radiation is transmitted through the fiber and deflected radially outwardly by the scattering material;

coupling said fiber an ultraviolet radiation source;

activating said radiation source to transmit radiation via said fiber and said diffusive tip assembly to irradiate the inner wall surfaces of the endoscopic instrument lumen; and retracting the fiber and diffusive tip assembly while continuing irradiation to expose a substantial length of the inner lumen surface to the ultraviolet radiation.

11. The method of claim 10 wherein the method further comprises delivering cytotoxic ultraviolet radiation via said fiber and diffusive tip assembly to the inner surfaces of the instrument lumen.

12. The method of claim 11 wherein the method further comprises employing ultraviolet radiation having a wavelength ranging from about 400 to about 200 nanometers.

* * * * *